US012582305B2

(12) United States Patent
Kamdar et al.

(10) Patent No.: US 12,582,305 B2
(45) Date of Patent: Mar. 24, 2026

(54) LIGHTED DISPOSABLE SPECULUM

(71) Applicant: Medline Industries, LP, Northfield, IL (US)

(72) Inventors: Neal Kamdar, North Brunswick, NJ (US); Bahram Kevin Kayvani, Chicago, IL (US); Yushek Pun, Dayton, NJ (US)

(73) Assignee: Medline Industries, LP, Northfield, IL (US)

( * ) Notice: Subject to any disclaimer, the term of this patent is extended or adjusted under 35 U.S.C. 154(b) by 439 days.

(21) Appl. No.: 18/101,214

(22) Filed: Jan. 25, 2023

(65) Prior Publication Data

US 2024/0245287 A1     Jul. 25, 2024

(51) Int. Cl.
| *A61B 1/06* | (2006.01) |
| *A61B 1/00* | (2006.01) |
| *A61B 1/32* | (2006.01) |

(52) U.S. Cl.
CPC ........ *A61B 1/0625* (2022.02); *A61B 1/00066* (2013.01); *A61B 1/00103* (2013.01); *A61B 1/0684* (2013.01); *A61B 1/32* (2013.01); *A61B 2560/0214* (2013.01)

(58) Field of Classification Search
CPC ........... A61B 1/32; A61B 3/0008; A61B 1/07; A61B 1/0684; A61B 1/00103
See application file for complete search history.

(56) References Cited

U.S. PATENT DOCUMENTS

| 10,368,733 B2 * | 8/2019 | Swift ..................... A61B 1/015 |
| 2002/0055670 A1 * | 5/2002 | Weiss ....................... A61B 1/32 |
| | | 600/220 |
| 2003/0187331 A1 * | 10/2003 | Faludi .................. A61B 1/0676 |
| | | 600/200 |
| 2012/0078060 A1 * | 3/2012 | Swift .................... A61B 1/303 |
| | | 600/219 |

(Continued)

FOREIGN PATENT DOCUMENTS

| CN | 103252015 A | 8/2013 |
| KR | 20120118618 A | 10/2012 |

(Continued)

OTHER PUBLICATIONS

International Search Report and Written Opinion; International Application No. PCT/US2024/012428; Medline Industries, LP; dated May 28, 2024.

(Continued)

*Primary Examiner* — Eduardo C Robert
*Assistant Examiner* — Holly Joanna Lane
(74) *Attorney, Agent, or Firm* — SandBright, PLLC; Robert D. Spendlove

(57) ABSTRACT

A disposable speculum with cordless light source can be used to facilitate visibility of an examination area during urological vaginal procedures and pelvic exams. The speculum features first and second light sources mounted at an angle to the yoke of the speculum thereby illuminating the examination area and providing the clinician an unobstructed line of sight. Additionally, the speculum has an improved adjustment mechanism and design that together alleviate the stress that accompanies the feel and sound of the speculum articulating during use.

15 Claims, 16 Drawing Sheets

(56)            References Cited

U.S. PATENT DOCUMENTS

| | | | |
|---|---|---|---|
| 2014/0275790 A1* | 9/2014 | Vivenzio .................. | A61B 1/06 |
| | | | 600/199 |
| 2015/0238070 A1* | 8/2015 | Lia ..................... | A61B 1/00034 |
| | | | 600/249 |
| 2016/0038012 A1* | 2/2016 | McMahon ............... | A61B 1/06 |
| | | | 600/210 |
| 2020/0069171 A1 | 3/2020 | Miller et al. | |
| 2022/0175239 A1* | 6/2022 | Vella ..................... | A61B 1/303 |

FOREIGN PATENT DOCUMENTS

| KR | 20140016030 A | 2/2014 |
|---|---|---|
| WO | 2006107878 A2 | 10/2006 |
| WO | 2006107878 A3 | 10/2006 |
| WO | 2018185742 A1 | 10/2018 |

OTHER PUBLICATIONS

Novelty Search Report, Dutch Patent Office, Application No. 2036803;
Medline Industries, LP; dated Jul. 10, 2024 (english at pp. 5-6).

\* cited by examiner

LIGHTED DISPOSABLE SPECULUM

FIELD OF THE INVENTION

The present invention relates generally to speculums and, in particular, to a disposable vaginal speculum with either a cordless light source or corded light bracket for facilitating urological procedures and pelvic exams.

BACKGROUND

A pelvic exam is often part of a routine physical screening to assess gynecological health including possible signs of ovarian cysts, sexually transmitted infections, uterine fibroids, or early-stage cancer. Pelvic exams are also commonly performed during pregnancy and in women experiencing unusual vaginal discharge or pelvic pain. At the start of the pelvic exam, a gynecologist or other clinician uses a speculum to open the walls of the vagina to better examine internal organs.

A speculum is a duck-bill-shaped device that clinicians use to see inside a hollow part of a patient's body to diagnose or treat disease. Commonly, speculums are made from stainless steel or plastic, wherein the steel variety are reusable while the plastic models are intended as disposable, single-use items. Vaginal speculums may have one or more blades for spreading the walls of the vagina apart and come in a variety of sizes and dimensions to accommodate use from small infants to larger adults.

Much advancement has been made in the art since the introduction of the modern vaginal speculum in the mid-nineteenth century, however, most of this progress is neither adapted to aid the clinician in directing light at the appropriate angle to improve internal visibility nor to fully improve the user experience during the pelvic exam.

A problem encountered during pelvic exams is the inability of the clinician to properly view internal organs with sufficient light and clarity without the aid of an assistant or the use of one hand to shine a flashlight into the examination area. Furthermore, the introduction of a flashlight within the narrow viewing angle of the examination area can obscure the clinician's view and diminish his or her capacity to properly examine, diagnose, and treat the patient. In addition, many patients experience discomfort and stress during pelvic examinations. The insertion and articulation of the speculum to open the vaginal canal is an invasive procedure that is often accompanied by sharp clicking sounds as the blades of the speculum are adjusted to the appropriate position. In the case of steel speculums, and indeed many plastic speculums, the feel and sound as the blades articulate results in a suboptimal patient experience, perhaps contributing to some women's and clinicians' hesitancy to receive or perform regular scheduled pelvic exams according to recommended healthcare guidelines.

Certain attempts have been made in the art to include a light source in conjunction with speculums. For example, incandescent light bulbs have been employed to illuminate the examination or surgical area. Still, incandescent lights release heat that can warm portions of the speculum and cause discomfort to the patient during use. Alternatively, other light sources and orientations have been contemplated, but such integrations of light sources tend to either obscure the clinician's line of sight with the examination or surgical area or fail to direct sufficient light to the proper location.

Accordingly, a need exists for a disposable speculum that provides the user with a beam of light that enables improved internal visibility and resultant enhanced diagnosis. Moreover, the patient experience could be improved through a disposable speculum having an improved adjustment mechanism and ergonomic design that together alleviate the stress that accompanies the feel and sound caused by articulating the speculum during a urological vaginal exam.

BRIEF DESCRIPTION OF THE DRAWINGS

The foregoing and other advantages of the invention will become apparent upon reading the following detailed description and upon reference to the drawings.

Figure 1:
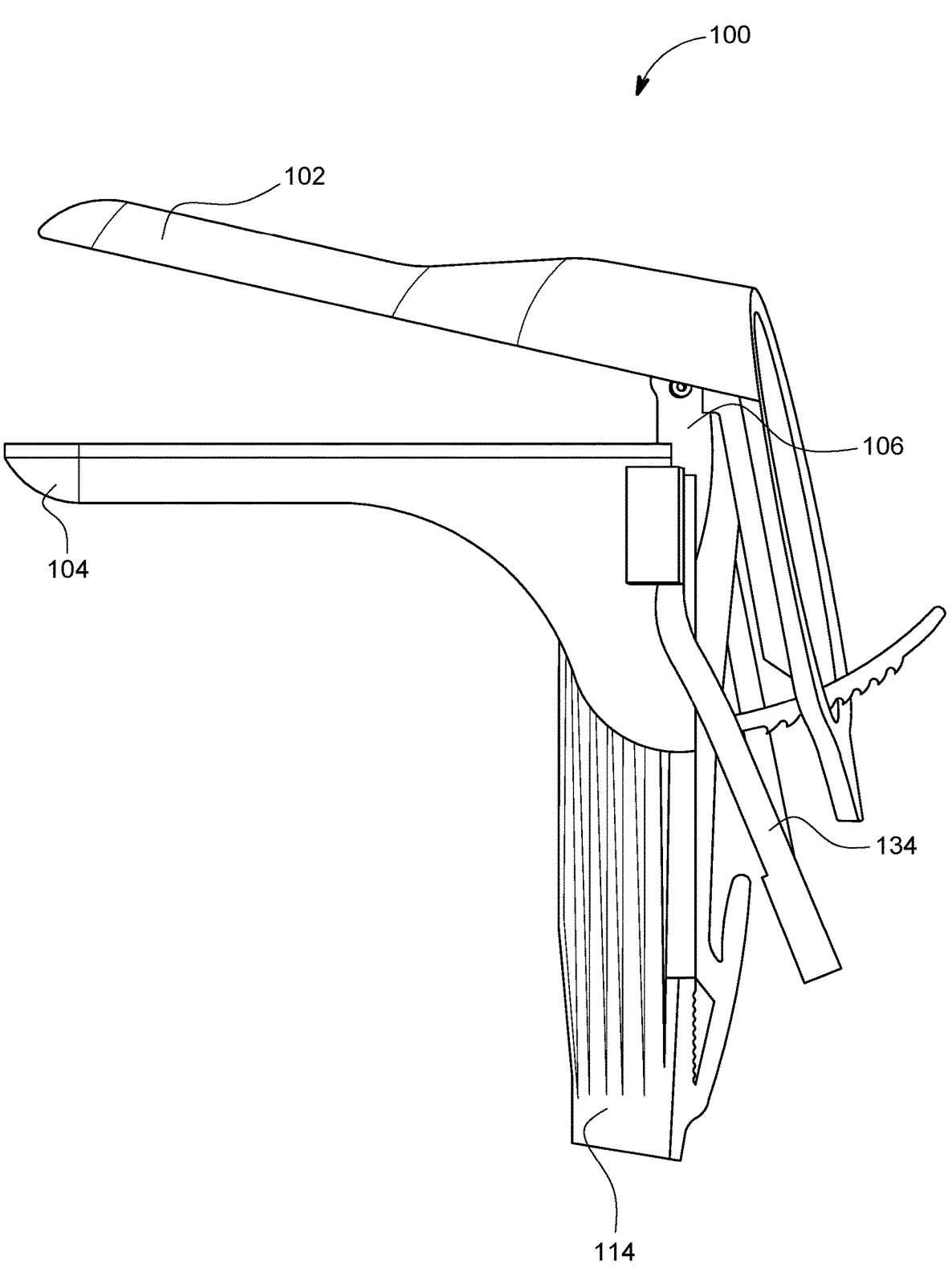
FIG. 1 is a side elevation view of an embodiment of a disposable speculum.
Figures 2, 3, 4:
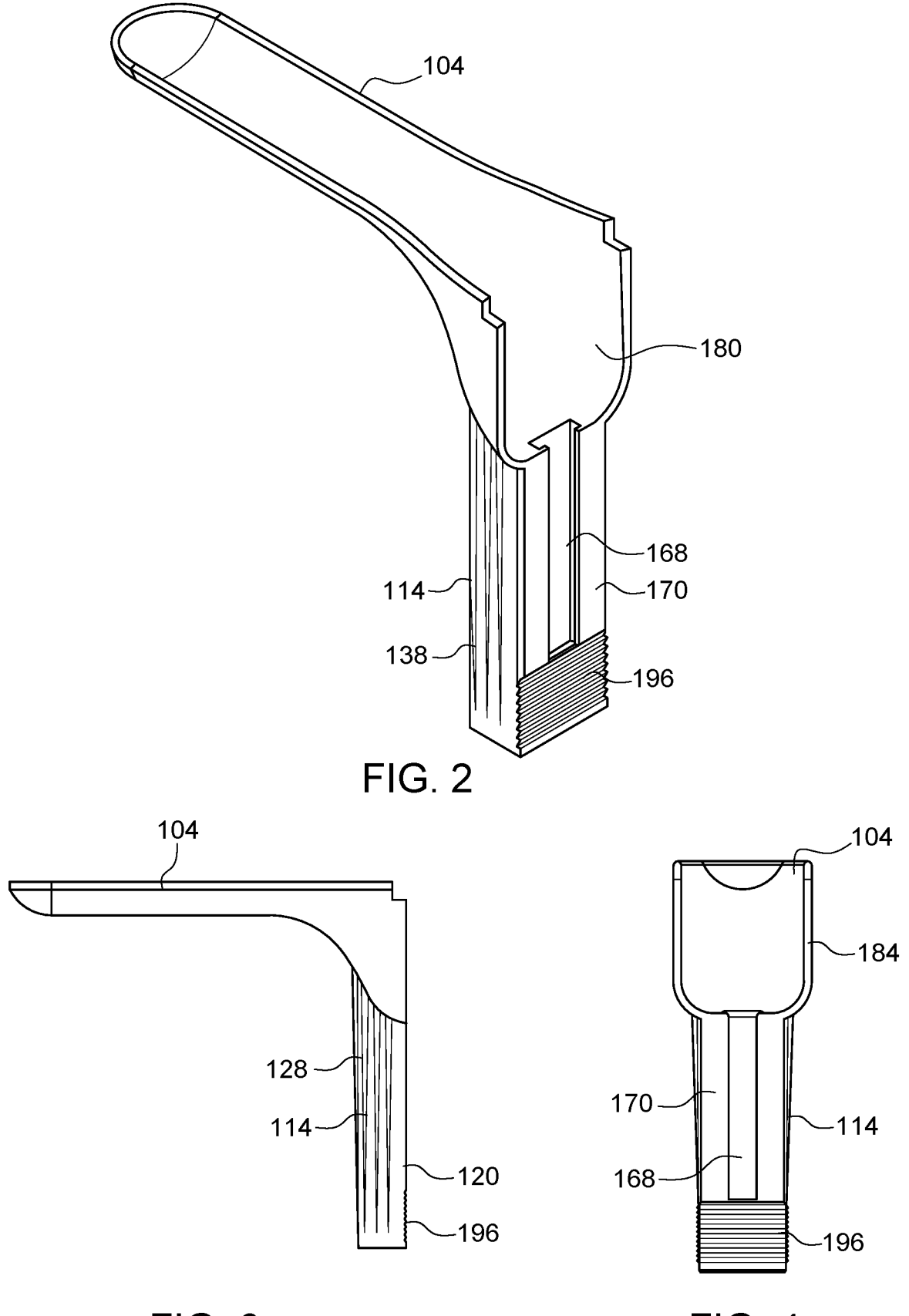
FIG. 2 is a rear side perspective view of a lower blade and handle of an embodiment of a disposable speculum.
FIG. 3 is a side elevation view of the lower blade and handle of FIG. 2.
FIG. 4 is a rear elevation view of the lower blade and handle of FIG. 2.
Figures 5, 6, 7:
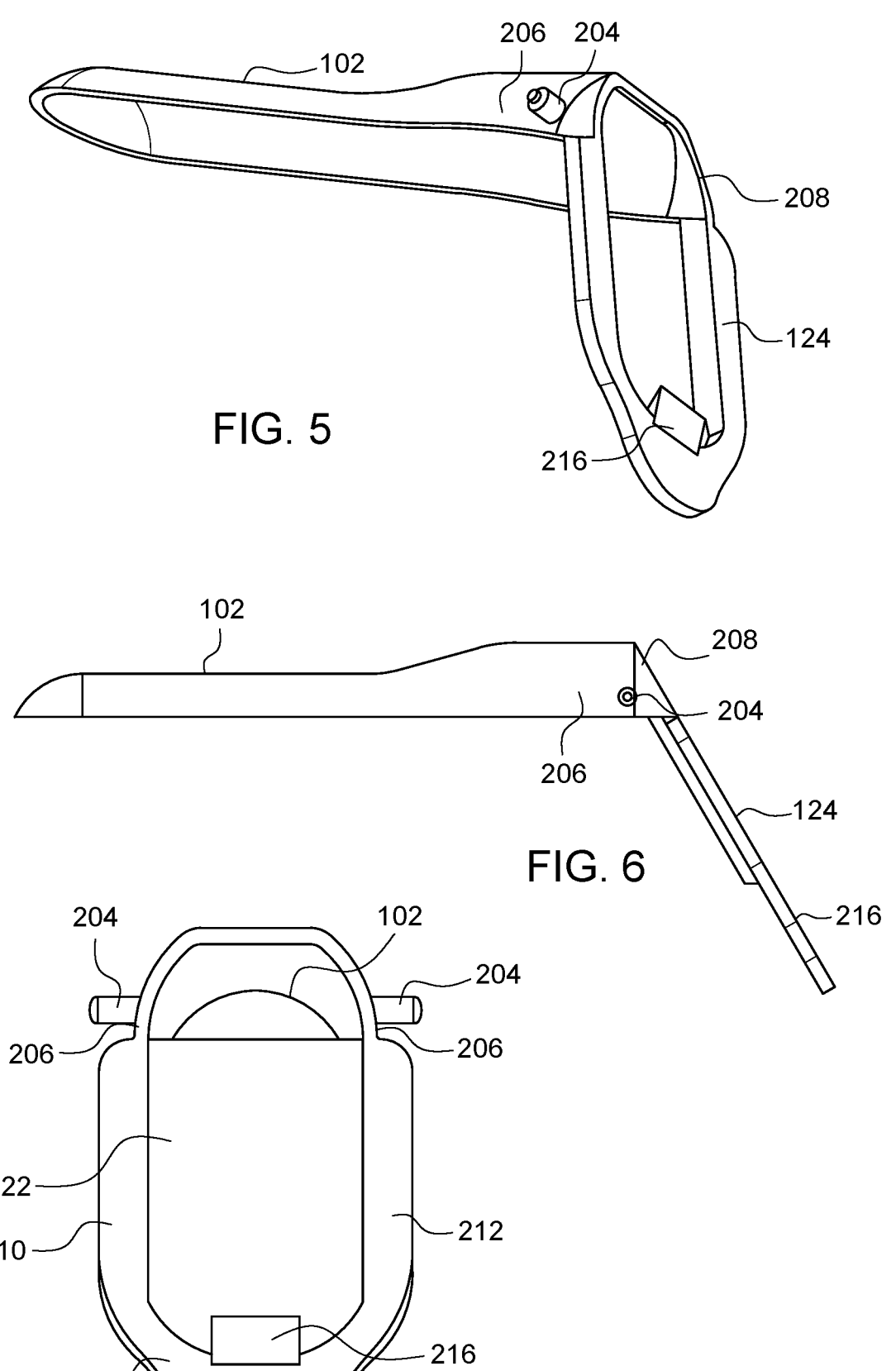
FIG. 5 is a rear perspective view of an upper blade of an embodiment of a disposable speculum.
FIG. 6 is a side elevation view of the upper blade of FIG. 5.
FIG. 7 is a rear elevation view of the upper blade of FIG. 5.

The drawings listed above are intended to convey to one of ordinary skill in the art the present invention and its embodiments. In some drawings certain elements have not been shown for clarity. While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. The following description of various embodiments, as represented in the figures, is not intended to limit the scope of the present disclosure but is merely representative of various embodiments. Reference throughout this specification to features, advantages, or similar language does not imply that all the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Referring to the drawings, like numbers generally indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, proximal and distal, posterior and anterior, and the like may be used solely to distinguish one entity or action from another entity or action without necessarily requiring or implying any actual such relationship or order between such entities or actions.

Additionally, instances in this specification where one element is "coupled to another element" can include direct and indirect coupling. Direct coupling can be defined as one element coupled to and in some contact with another element. Indirect coupling can be defined as coupling between two elements not in direct contact with each other but having one or more additional elements between the coupled elements. Further, as used herein, securing one element to another element can include direct securing and indirect securing. Additionally, as used herein, "adjacent" does not necessarily denote contact. For example, one element can be adjacent to another element without being in contact with that element. In addition, the term "clinician" is used herein to indicate the medical practitioner or any other person that may utilize a speculum. The term is not intended to be limiting on the scope of the described or claimed embodiments.

FIG. 1 illustrates an exemplary non-limiting general embodiment of a disposable speculum 100. Specifically, FIG. 1 illustrates a side elevation view of the disposable speculum 100 in an open configuration. As shown in this figure, the disposable speculum 100 generally comprises two or more blades, a handle, an adjustment mechanism, a light source, and a power source. Non-limiting examples of materials suitable to manufacture the disposable speculum include polypropylene, polyethylene, polycarbonate, related polymers and materials having medical-grade certification, combinations thereof and/or the like.

As illustrated in FIGS. 1-11, embodiments of the disposable speculum 100 may comprise a posterior or upper blade 102 and an anterior or lower blade 104. The upper 102 and lower 104 blades may be connected by a yoke 106. The yoke 106 may comprise a base 108, a first arm 110 extending upwardly from the base 108, and a second arm 112 extending upwardly from the base with the second arm parallel to and spaced apart from the first arm. A leg 166 may extend downwardly from the base 108 of the yoke 106 such that the base 108, first arm 110, second arm 112, and leg 166 of the yoke form a general "Y" shape.

A handle 114 may extend downwardly at a substantially right angle from the lower blade 104. The handle 114 may comprise a slot 168 formed on a rear surface 170. The yoke 106 may comprise a corresponding slot 174 formed on a side surface 176 of the yoke leg 166. The blade handle slot 168 and yoke slot 174 may slidably engage one another to secure the lower blade to the yoke. The yoke may comprise a stepped section 178 adjacent to the yoke base 108 that corresponds to a widened section 180 of the lower blade 104 such that the yoke base 108 sits within a cavity of the lower blade 104 at the widened, rearward section of the blade when the yoke and blade are assembled. A flange 182 of the yoke stepped section 178 may extend and cover at least a portion of a rear surface 184 of the lower blade 104.

A latch 136 may extend from a rear surface 186 of the yoke leg 166. The latch may comprise a post 188 that allows the latch to flex between latched and unlatched positions when a pad 190 of the latch is pressed. The pad 190 may comprise grip elements 192. The latch 136 may further comprise a tip or pawl 194 that engages notches 196 formed on the rear surface 170 of the lower blade handle 114. Consistent with such embodiments, a clinician may press the pad 190 and pivot the latch 136 by flexing of the post 188. This pivoting motion removes the pawl 194 from a notch 196 in the handle 114. The yoke and handle slots may then slide relative to one another. The latch may be biased toward engagement with the notches 196 such that when the pad is released, the pawl engages a different notch. In this manner, a clinician may adjust the distance between the top of the yoke, and therefore the upper blade, and the lower blade.

Upper ends 198, 200 of first and second arms 110, 112 may comprise transverse holes 202. These holes 202 may engage tabs or axles 204 extending from side surfaces 206 of the upper blade 102. In this way, the upper blade 102 may be pivotally mounted to the yoke 106 such that the blade may be rotated, thereby opening and closing the blades 102, 104 of the speculum 100. A collar 124, or other appropriately shaped member, may extend from a rearward end 208 of the upper blade 102. The collar may comprise first and second side legs 210, 212. A cross member 214 may connect the two side legs. A pawl or protrusion 216 may extend from the cross member 214. The protrusion may engage an adjustment post 116 that extends from the rear surface 186 of the yoke leg 166. The yoke post 116 may comprise a plurality of slots 122 angled along a rear or lower surface 218 of the post 116. The upper blade collar 124 may be configured to interlock and fasten at various points along the corresponding plurality of slots 122 on the yoke post 116. The yoke post may be curved to accommodate the rotational movement of the upper blade 102 relative to the yoke 106 and lower blade 104.

In practice, a distal tip of the yoke post 116 may be passed through an opening 222 of the collar 124 until the protrusion 216 of the collar 124 engages with the plurality of slots 122 on the yoke post 116. The clinician may progressively widen the mouth of the upper and lower blades 102, 104 to an appropriate open configuration. As determined by the clinician, the protrusion 216 of the collar 124 may be fit to the appropriate setting along the plurality of slots 122 during the pelvic examination and thereafter disengaged by lifting the yoke post 116 upwards to disengage the protrusion 216 and return the disposable speculum 100 to a closed configuration. The yoke post 116 may alternatively comprise a hook and loop, snaps, or any other appropriate fasteners as would be understood by one of ordinary skill in the art.

A first light source 118 may be coupled to the first arm 110 and a second light source 120 may be coupled to the second arm 112. The first and second light sources 118, 120 may be LED lights. Moreover, the LED lights may be 5 mm dome LEDs. The handle 114 is that portion of the disposable speculum 100 which, when the disposable speculum 100 is held, is generally positioned within the hand of the clinician, and the handle 114 may comprise an ergonomic handle. In some embodiments, the handle 114 may feature a wide body having a plurality of ridges 138 along a longitudinal axis of the handle that may provide additional surface area and ease of grip by the clinician.

The upper and lower blades 102, 104 together form a duckbill shape such that the interior is hollow, and the exterior is conical or at least substantially conical having a rounded tip on a distal end as shown in the illustrative embodiment of the disposable speculum 100. In other embodiments, there may be portions of the upper and lower blades 102, 104 that are shaped more broadly or narrowly at certain sections, resulting in a contoured fit within the vaginal canal. Still other embodiments have different shaped upper and lower blades 102, 104 with varying lengths, such as Pederson, Graves, Huffman, and alternative versions of speculums known in the art to accommodate the fit of the disposable speculum 100 to the circumstances of infants, teenage girls, and larger adults. It will be appreciated that the upper and lower blades 102, 104 may be manufactured from clear, transparent polymers permitting the clinician to continuously view more surface area of the vaginal canal without obstruction.

As illustrated in FIGS. 8-12, a first battery housing 126 may be coupled to an exterior surface 111 of the first arm 110 of the yoke 106. Likewise, a second battery housing 128 may be coupled to an exterior surface 113 of the second arm 112 of the yoke 106. The battery housings 126, 128 may each feature batteries 220 connected to leads 140 that power the respective first and second light sources 118, 120. The batteries may comprise two 1.5V alkaline cell batteries or any other appropriate batteries as would be understood by a person of ordinary skill in the art. The first battery housing 126 may comprise a first cover plate 130, and the second battery housing 128 may comprise a second cover plate 132 (removed for visibility in FIGS. 8 and 11). The battery housings may also comprise first and second conductive plates 222. The conductive plates may comprise nickel or other conductive material as would be apparent to one of ordinary skill.

The leads 140 of the respective first and second light sources 118, 120 may be electrically couplable to the conductive plates, wherein when the leads 140 are electrically coupled to the conductive plates, the first and second light sources 118, 120 are illuminated and when the leads 140 are not coupled to the nickel plate, the first and second light sources 118, 120 are not illuminated. In some embodiments, the disposable speculum 100 may also comprise a tab 134 that is inserted between the conductive plate and the batteries in each of the battery housings 126, 128. The tab may comprise a first section 134a having a first end that is inserted between the conductive plate and the lead at the first battery housing and a second section 134b having a corresponding first end that is inserted between the conductive plate and the lead at the second battery housing. The tab may be Y-shaped such that the first and second sections 134a, 134b are connected at second ends to form a joined section 134c. Thus, a clinician may grasp the Y-shaped tab 134 at the joined section pull out the Y-shaped tab 134 to turn on the first and second light sources 118, 120. Apertures 131a, 131b may extend through a surface of the first and second housings 126, 128 to allow passage of the pull tab 134. In embodiments of the speculum, these apertures extend through the first and second housings in a direction generally parallel to the handle 114 or yoke leg 166 such that the tab can be removed by pulling it a direction generally parallel to the handle 114. It will be appreciated that the disposable speculum may be packaged, shipped, and stored for prolonged periods of time with the Y-shaped tab inserted to ensure the light sources remain off before use by a clinician while conserving the batteries. At the time of use, the clinician may remove and discard the plastic Y-shaped tab 134 to permit the light sources of the disposable speculum 100 to be turned on.

The disposable speculum 100 may comprise a rear surface 226 of the first arm 110 of the yoke 106 having an aperture 224 through which the first light source 118 may be fastened through hot glue, screws, compression fit, or other comparable fastening mechanism known in the art. Likewise, a rear surface 230 of the second arm 112 of the yoke 106 may have an aperture 232 through which the second light source 120 may be fastened. The apertures 224, 232 may be formed in extensions 225, 233 that extend inwardly from first and second arms 110, 112. Leads 140 may comprise a first pair of side connectors having a first lead 140a extending through a first aperture in the first housing 126 to connect with the first light source 118 and a second lead 140b extending between the light source 118 and the battery housing 126 through a second aperture. Leads 140 may further comprise a second pair of side connectors having a third lead 140c extending through a third aperture in the second housing 128 to connect with the second light source 120 and a fourth lead 140d extending between the light source 118 and the battery housing 128 through a fourth aperture. Alternatively, each pair of side connectors may extend through a common aperture. Leads 140 may comprise any appropriate conductive material. The cover plates 130, 132 may be coupled to the respective first and second battery housings 126, 128 by a flexible polymer member, hot glue, a spring, or similar means of attaching the cover plates to the battery housings.

The speculum may comprise an upper blade 102 that may be coupled to the first and second arms 110, 112 of the yoke 106 via pin joints such as hinges or roller bearings thus permitting the relative rotation of the posterior blade 102 about a single axis when actuated by the clinician between the closed configuration and the open configuration. By contrast and for ease of manufacture, the lower blade 104 may be fixed to the yoke 106 at a ninety-degree, perpendicular angle. The upper blade may also be manufactured as one continuous, integrated piece of polymer with the ergonomic handle 114.

Figure 8:
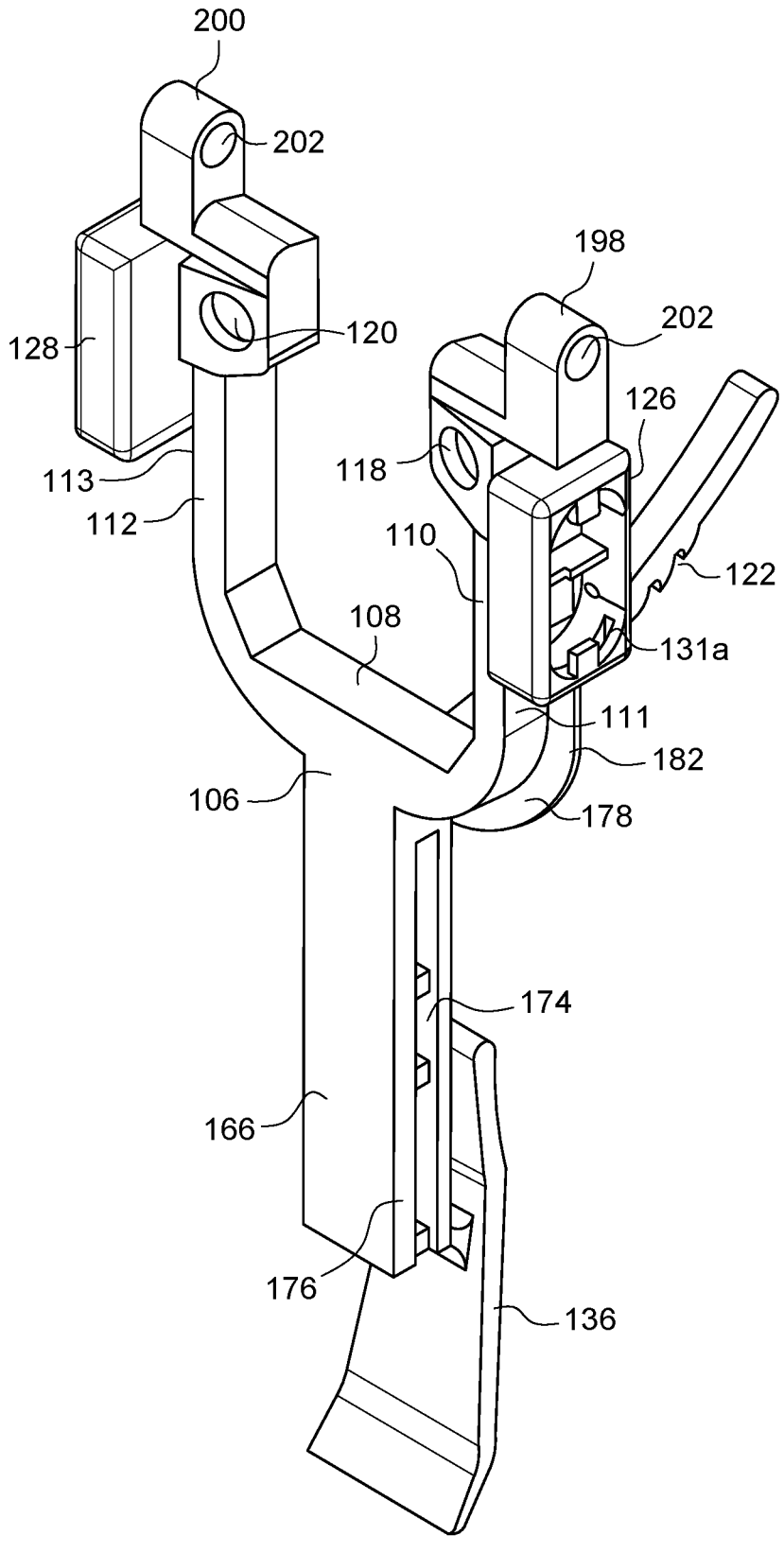
FIG. 8 is a front perspective view of a yoke of an embodiment of a disposable speculum.
Figure 10:
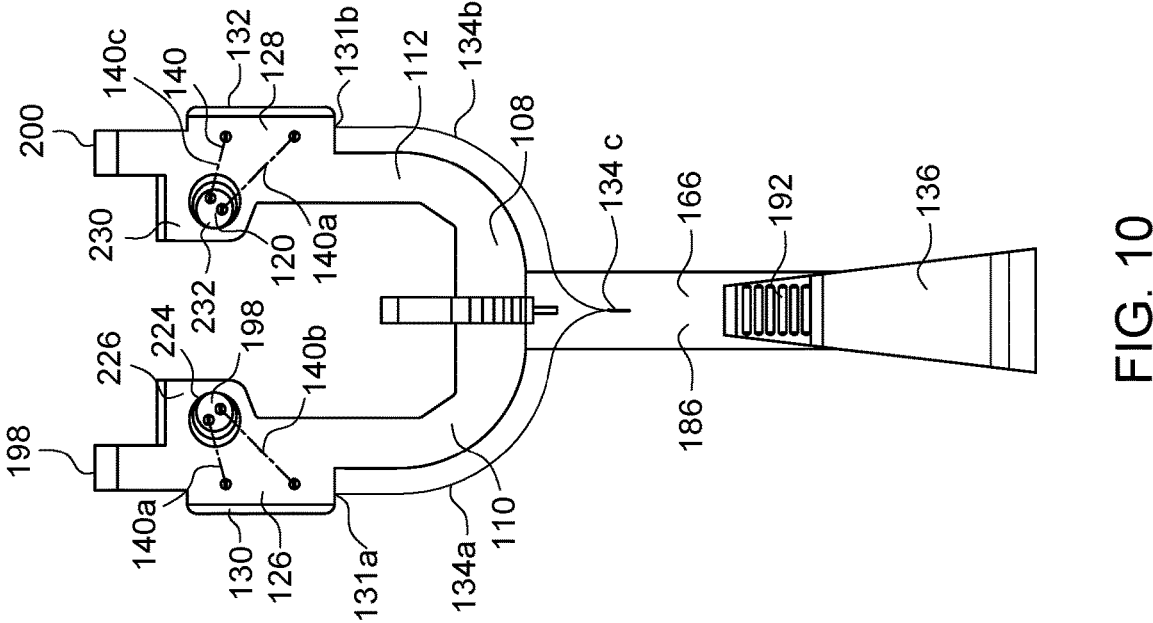
FIG. 10 is a rear elevation view of the yoke of FIG. 9.
Figure 9:
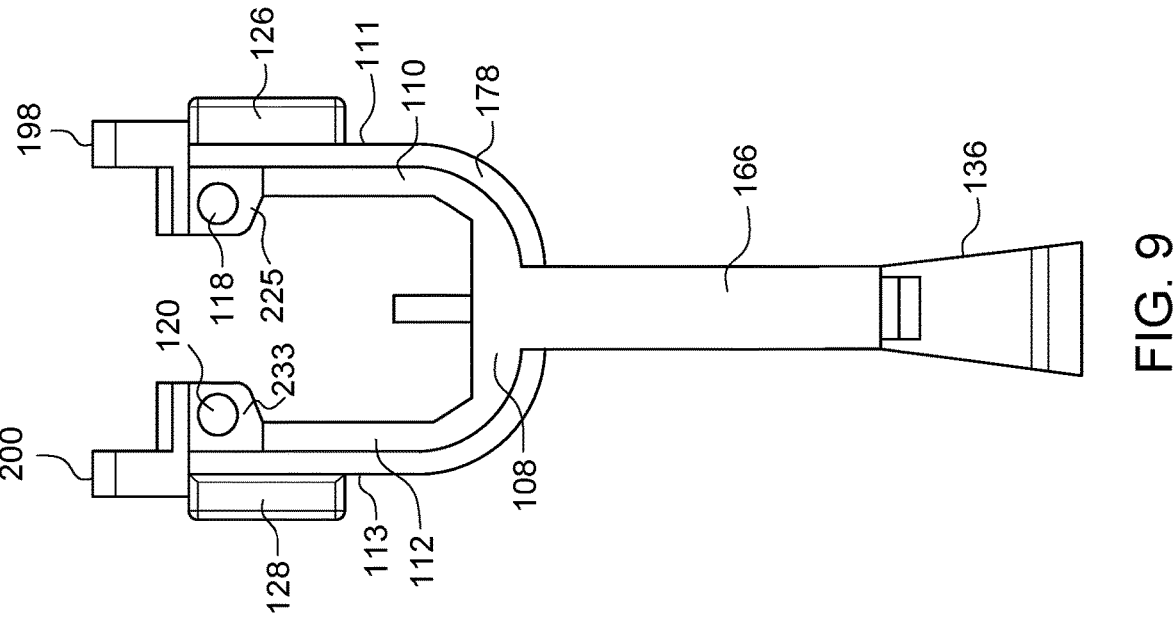
FIG. 9 is a front elevation view of the yoke of FIG. 9.
Figure 11:
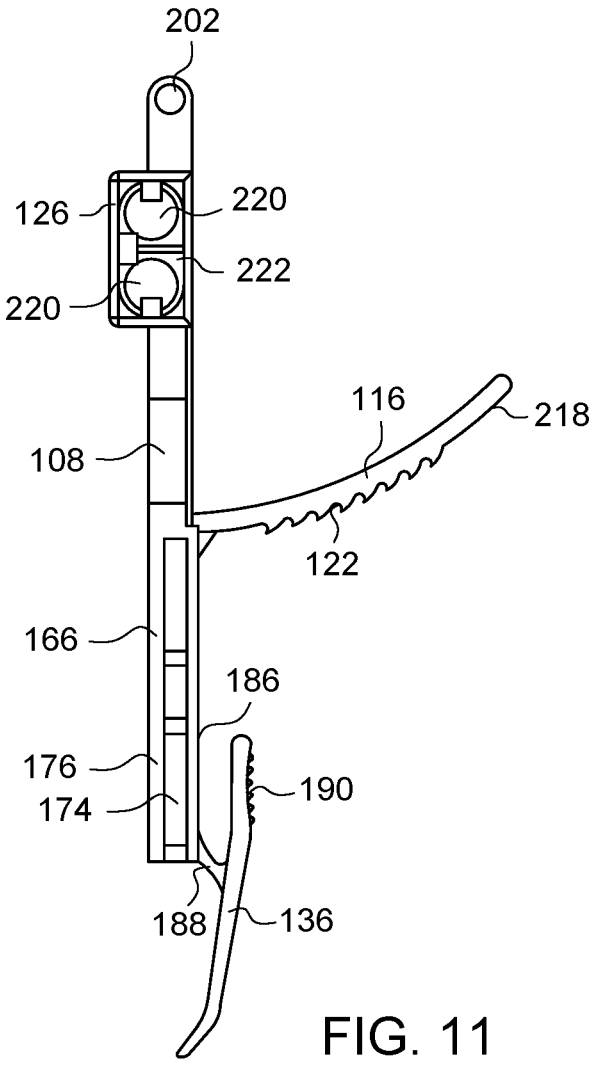
FIG. 11 is a side elevation view of the yoke of FIG. 9.
Figure 12:
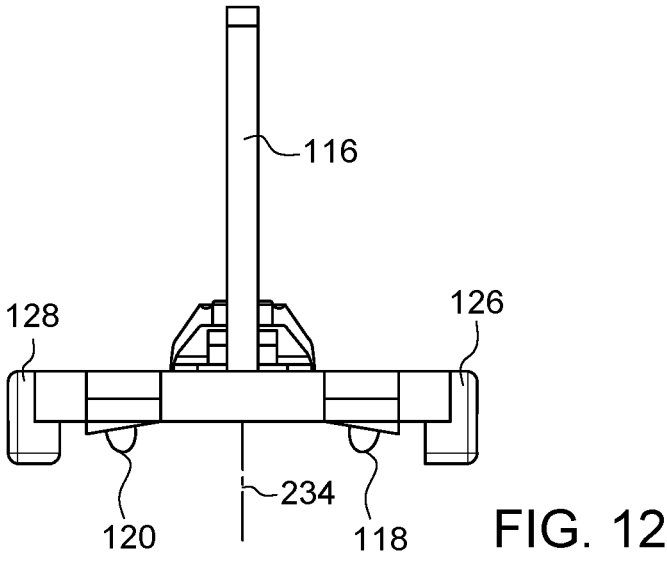
FIG. 12 is a top plan view of the yoke of FIG. 9.
Figure 14:
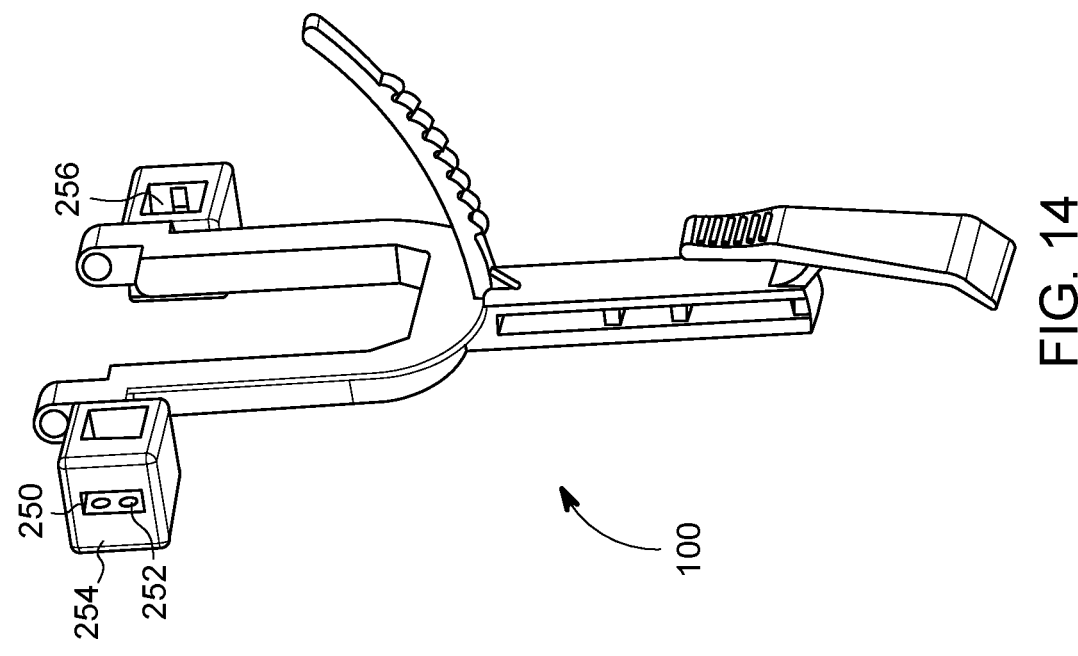
FIG. 14 is a rear perspective view of the yoke of FIG. 13.
Figure 13:
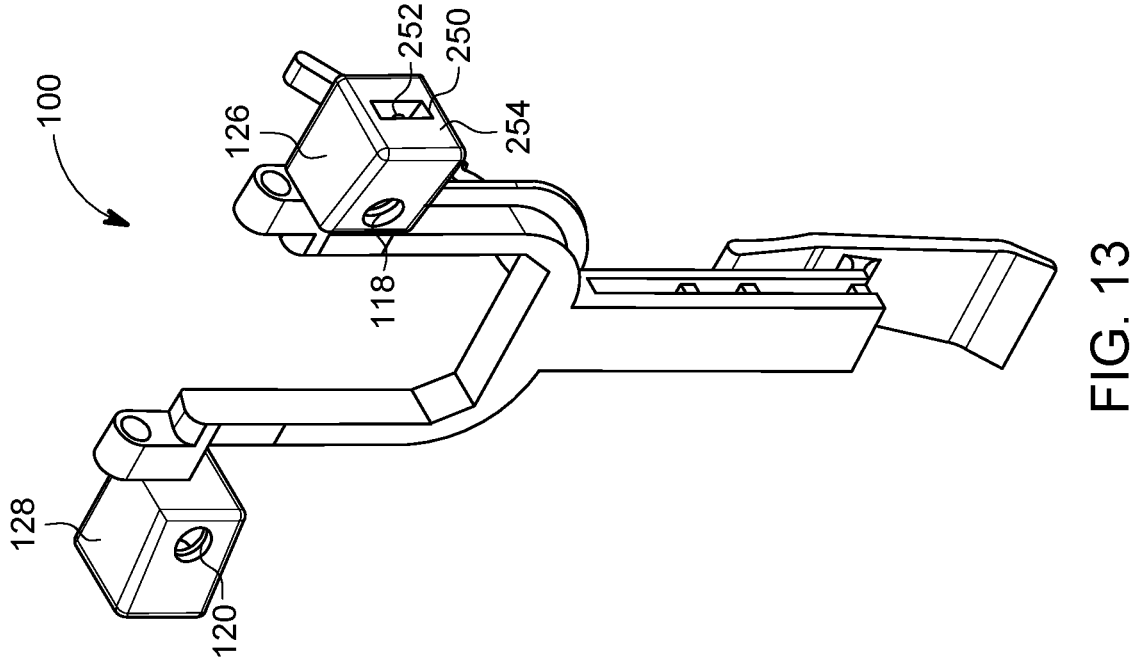
FIG. 13 is a front perspective view of a yoke of a further embodiment of a disposable speculum.
Figures 15, 16:
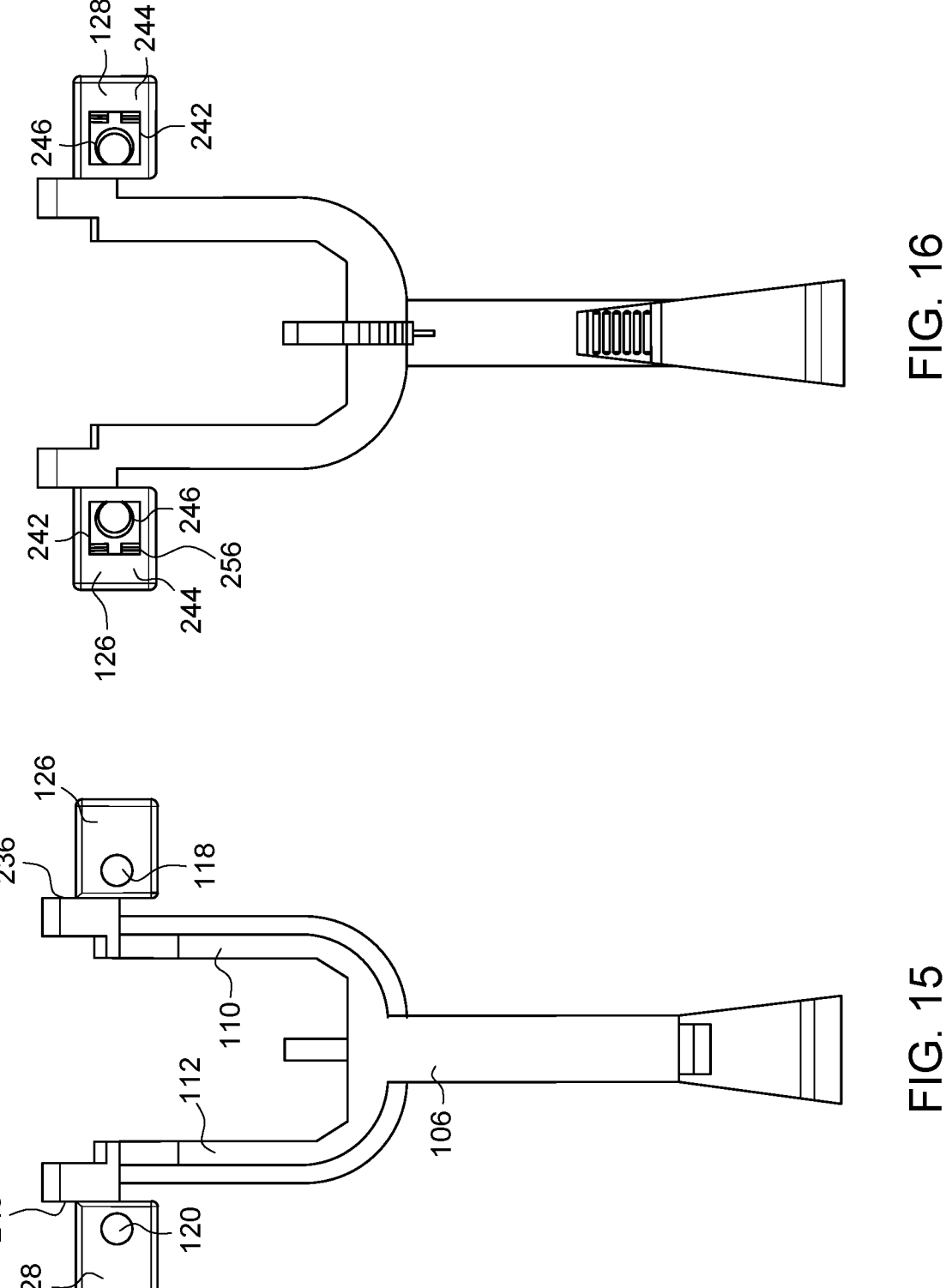
FIG. 15 is a front elevation view of the yoke of FIG. 13.
FIG. 16 is a rear elevation view of the yoke of FIG. 13.
Figure 17:
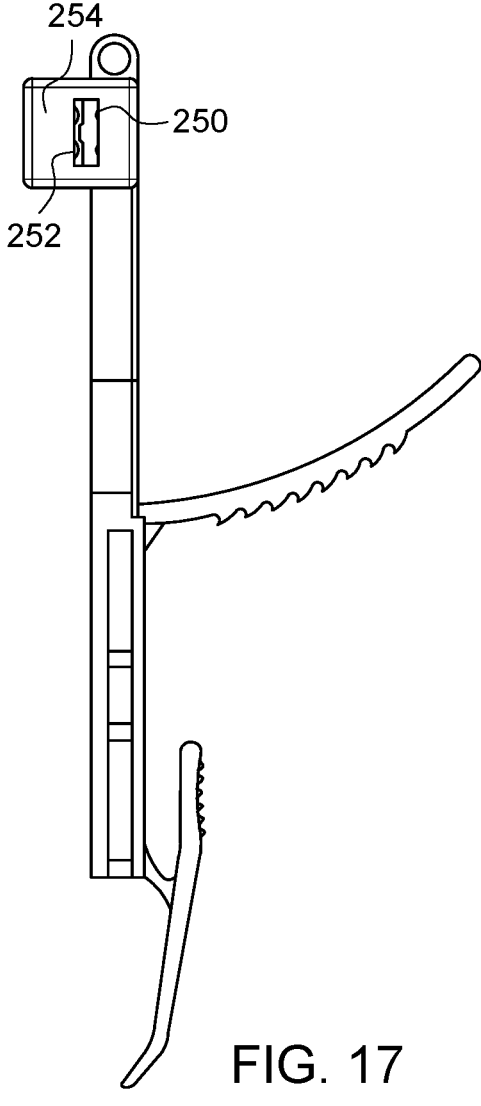
FIG. 17 is a side elevation view of the yoke of FIG. 13.

As illustrated in FIGS. 8-12 and particularly in FIGS. 8 and 12, the first and second lights sources 118, 120 when mounted along the interior sides of the first and second arms 110, 112 of the yoke 106 may directly illuminate the examination area at the distal end of the posterior and anterior blades 102, 104. In embodiments of the speculum, the first and second lights sources 118, 120 may be angled towards a centerline 234 of the disposable speculum 100 extending to the examination area thereby optimizing the visibility within the vaginal canal during use. Without limiting the invention, an optimal angle for the first and second lights sources 118, 120 may range between five degrees and thirty degrees depending on where within the examination area the clinician is required to focus the emitted light. For example, an angle of fifteen degrees provides significant convergence of the emitted light to a focused beam that illuminates the entire examination area. It will be appreciated that a distance between the first and second lights sources 118, 120 combined with a distance between the upper and lower blades 102, 104 provide a wide cross-sectional area through which the clinician may have a clear and direct line of sight from the rear of the disposable speculum 100 to the examination area.

As illustrated in FIGS. 13-17, embodiments of the disposable speculum comprise first and second light sources 118, 120 may be coupled to the first and second arms 110, 112 of the yoke 106. A first battery housing 126 may be coupled to an exterior surface 236 of the first arm 110 of the yoke 106. Likewise, a second battery housing 128 may be coupled to an exterior surface 240 of the first second arm 112 of the yoke 106. Covers (removed for illustration) may cover openings 242 formed in rear surfaces 244 of the first and second housings 126, 128. Apertures 246 may extend through front surfaces 248 of the housings 126, 128 to allow light sources 118, 120 to protrude or shine through. The battery housings 126, 128 may each comprise one or more batteries. The batteries may be connected with the light sources 118, 120 by leads positioned within the housings.

Compared with the embodiments illustrated in FIGS. 8-12, the embodiments of FIGS. 13-17 the overall cross-sectional area within the first and second arms 110, 112 of the yoke 106 may be wider and provide the clinician a more expansive view of the examination area. Accordingly, the first and second light sources 118, 120 within the first and second battery housings 126, 128 may be angled inwardly at a greater angle to account for the further distance of the first and second light sources 118, 120 from the centerline of the disposable speculum 100.

Figure 18:
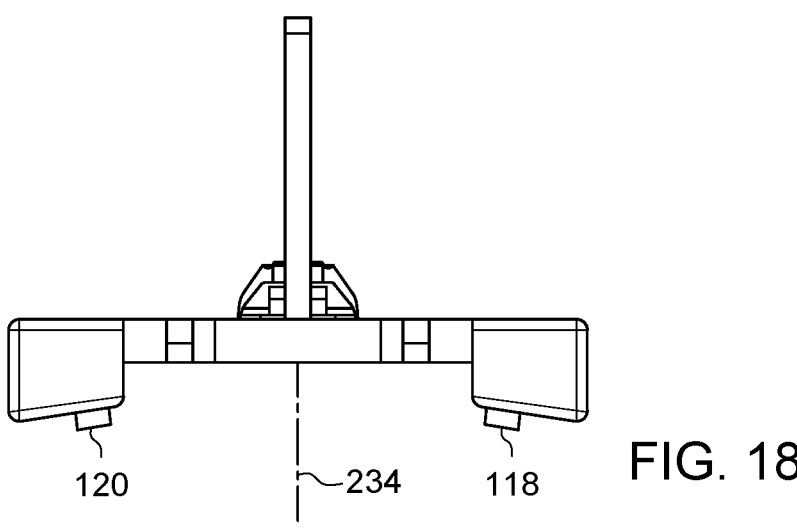
FIG. 18 is a top view of the yoke of FIG. 13.
Figure 19:
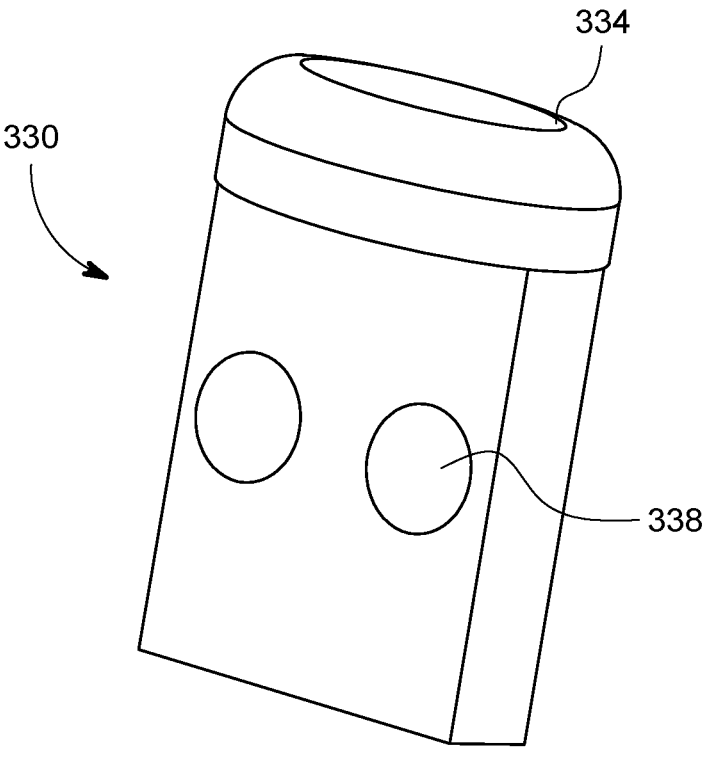
FIG. 19 is a perspective view of a push key for use with embodiments of the yoke of FIG. 13.
Figure 20:
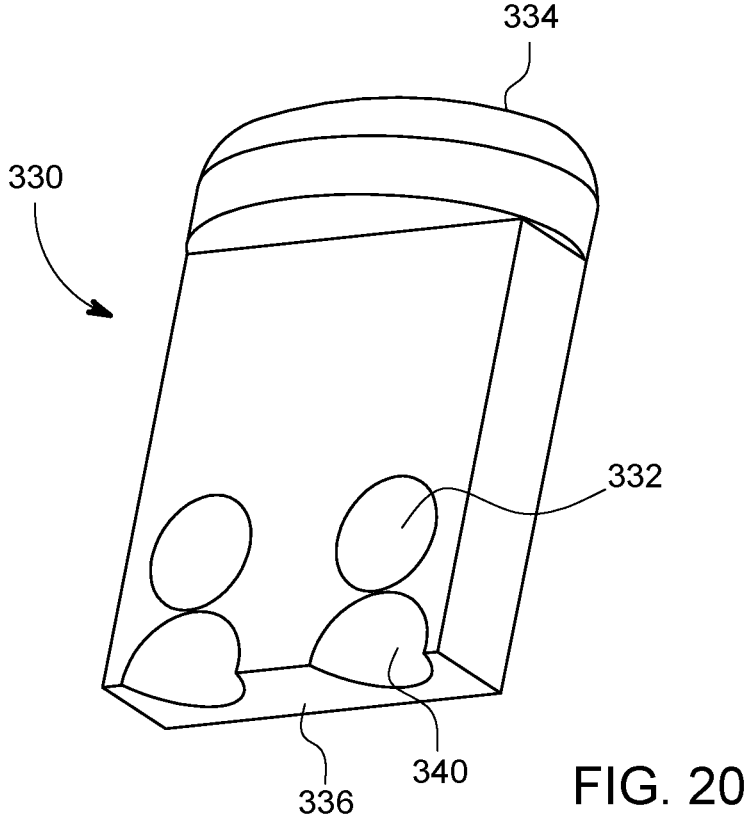
FIG. 20 is a further perspective view of the push key of FIG. 19.
Figures 21, 22:
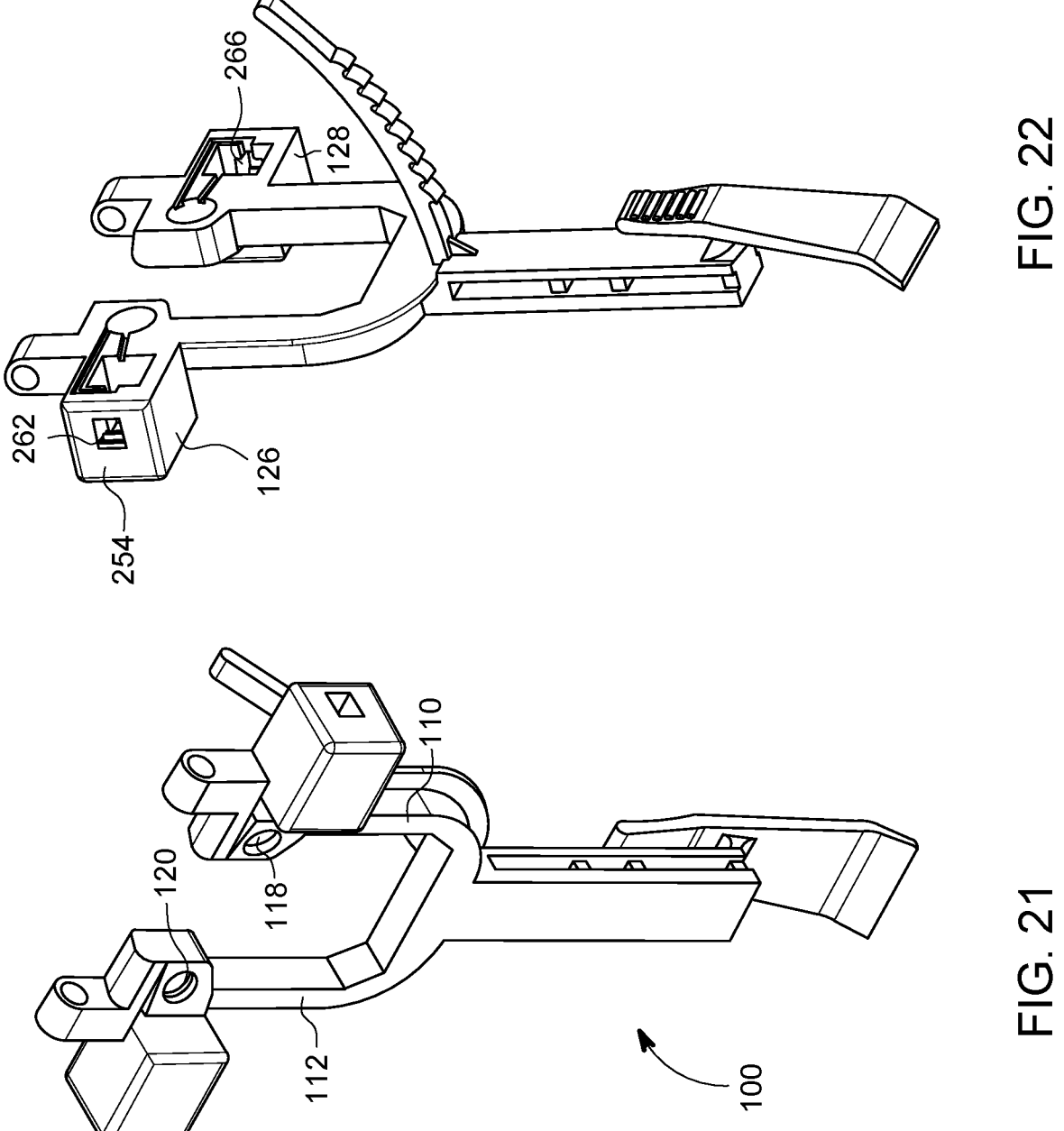
FIG. 21 is a front perspective view of a yoke of a further embodiment of a disposable speculum.
FIG. 22 is a rear perspective view of the yoke of FIG. 21.
Figures 23, 24:
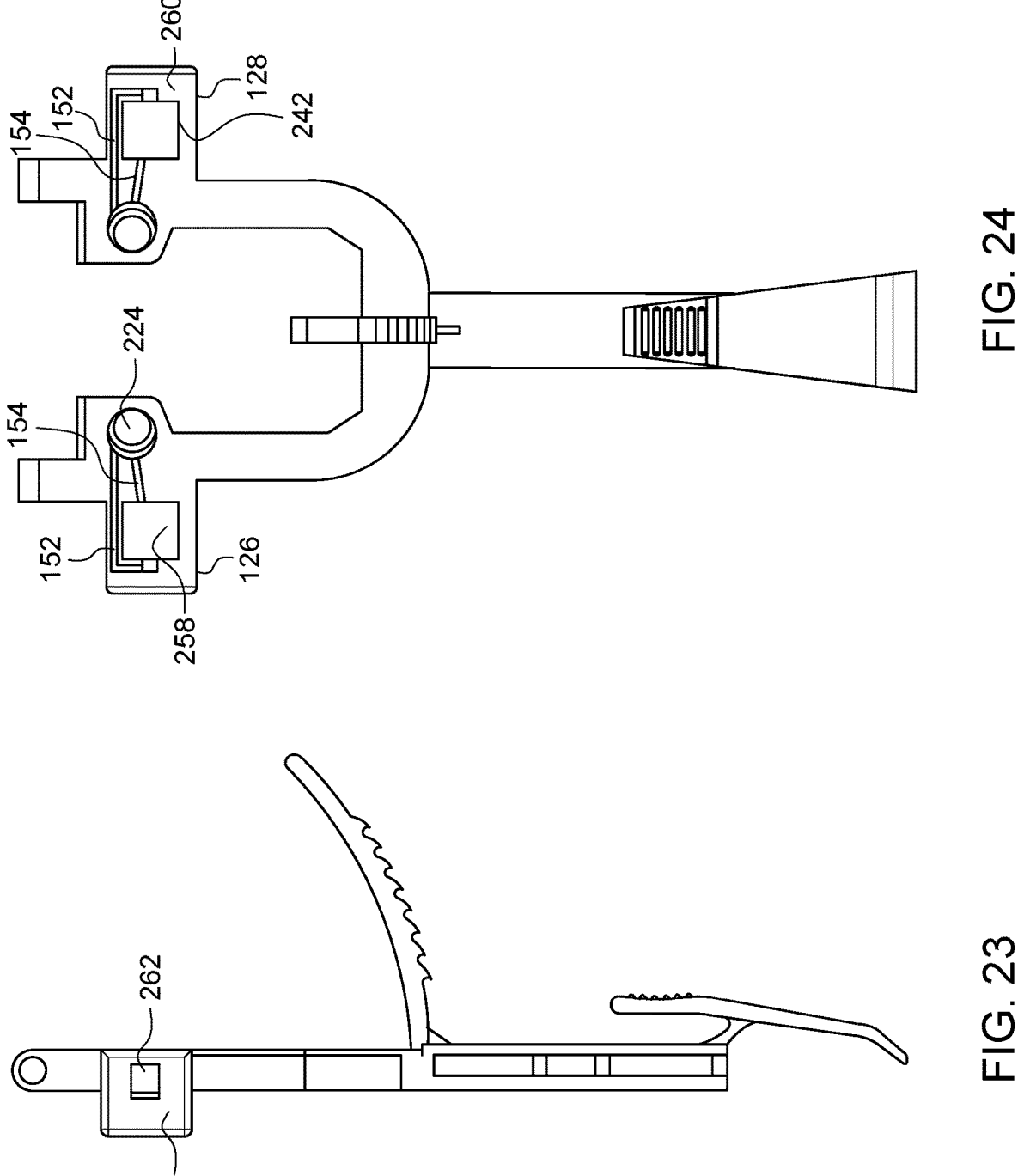
FIG. 23 is a side elevation view of the yoke of FIG. 21.
FIG. 24 is a rear elevation view of the yoke of FIG. 21.

Embodiments of the battery housings 126, 128 may each comprise a slot 250 formed in an outer surface of the housing. For example, the slot 250 may be formed in a lateral side surface 254 of the housing 126. An interior of the slot may comprise one or more protrusions 252. The housing may also comprise a conductive plate 256. The conductive plate may be spring biased away from contact with the battery or a connected lead. The spring bias of the plate may be provided by a separate spring or by a resilient flexibility of the spring itself. The speculum 100 may further comprise a push key 330 as illustrated in FIGS. 18-19. The push key 330 may be sized to slidably engage the slot 252 of the housing 126 and may comprise a first detent 332 that engages with a protrusion 252 of the housing slot 250. The first detent may hold the push key in a first, extend or inactive position. Embodiments of the speculum may be shipped with the push key in the inactive position.

The push key may comprise a button 334 that allows a user to push the key from the inactive position to a retracted, active position. In the active position, an end surface 336 of the key is pressed against the conductive plate 256 and overcomes the spring bias of the plate such that the plate electrically connects with the battery, thereby providing electrical power to the light source 118. Alternatively, one or more batteries may be spring biased away from electrical connection and moving the push key to the active position may move the battery into electrical connection.

The push key may comprise a second detent 338 that engages with the same or different protrusions 252 of the housing 126. The second detent thus secures the push key against returning to the inactive position. The first and second detents may be on opposite sides of the key as illustrated in FIGS. 18-19 or on the same side of the key. The key 330 may also comprise a ramp portion or partial detent 340 that aids in inserting the key past the first detent when the speculum is assembled.

Referring to FIGS. 21-24, the disposable speculum 100 may comprise the first and second light sources 118, 120 mounted on the interior of the first and second arms 110, 112 of the yoke 106 and the first and second battery housings 126, 128 mounted on the exterior of the first and second arms 110, 112 of the yoke 106, according to embodiments of the speculum. The first light source 118 and the second light source 120 may be angled inward towards the front of the disposable speculum 100 being configured to converge emitted light into a focused beam on the examination area. The first battery housing 126 is positioned on the exterior surface of the first arm 110 of the yoke 106 and the second battery housing 128 is positioned on the exterior surface of the second arm 112 of the yoke 106.

Each battery housings 126, 128 of the disposable speculum 100 may further comprise a first channel 152 and a second channel 154. For example, the channels may provide conduits for electrical leads extending from a battery compartment 258 of the housing 126 to the aperture 224 through which the light source 118 extends and may electrically isolate the battery leads from the battery until activated. In particular, the first channel 152 may begin at a first surface of the batteries within a battery well of both the first and second battery housings 126, 128, extend across a rear surface of the battery housings 126, 128, and approach a base of the light sources 118, 120. The second channel 154 may begin at a second surface of the batteries within a battery well of both the first and second battery housings, extend across a rear surface of the first and second battery housings 126, 128, and approach a base of the first and second light sources 118, 120. Each of the first and second channels 152, 154 may comprise LED leads fitted within the contours of the first and second channels 152, 154. One of the leads may be a positive lead while the corresponding lead may be a negative lead. The disposable speculum 100 may further comprise a snap activation key or switch that engages the leads with the batteries thereby completing an electric circuit and turning the first and second light sources 118, 120 on. The snap key may be a cantilever snap push activation key. A cover plate (not shown) may be couplable to an aperture 242 on the rear surface 260 of each of the first and second battery housings 126, 128 to conceal the batteries and leads from inadvertent exposure.

Figure 25:
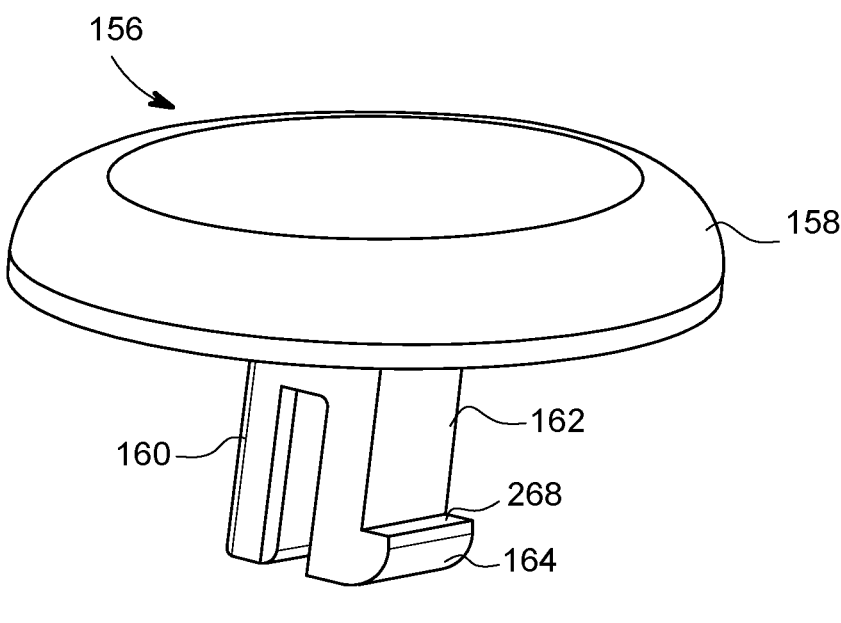
FIG. 25 is a perspective view of a snap key for use with embodiments of the yoke of FIG. 21.
Figure 26:
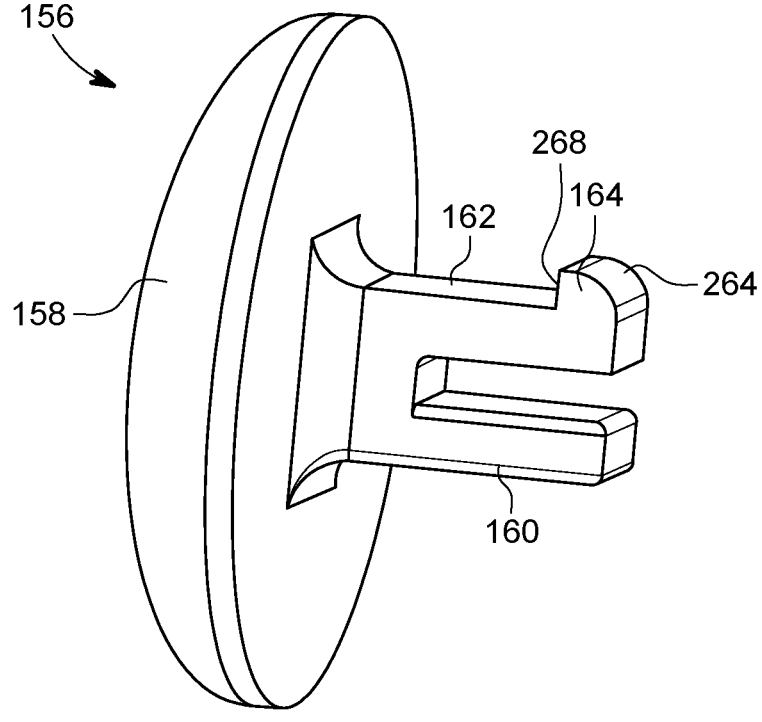
FIG. 26 is a further perspective view of the snap key of FIG. 25.
Figure 27:
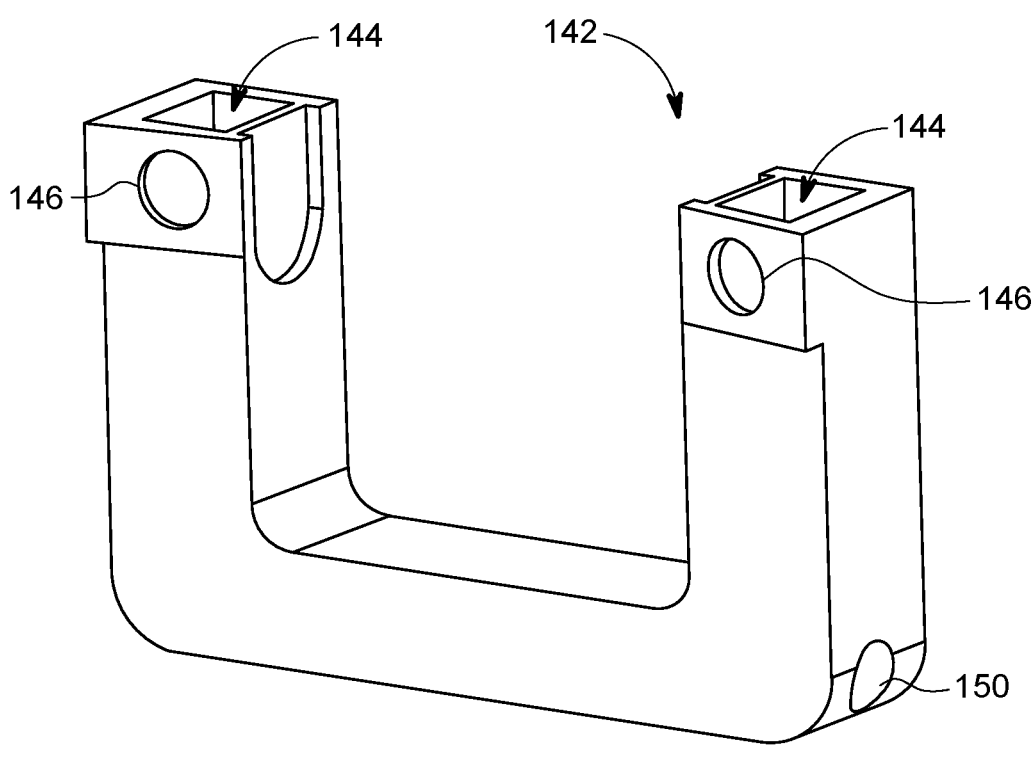
FIG. 27 is a perspective view of an embodiment of a lighted bracket attachable to a speculum.
Figure 28:
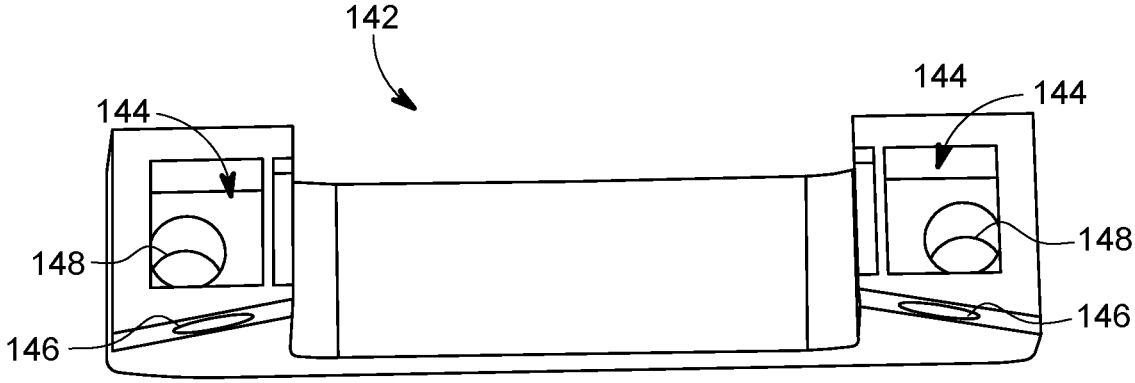
FIG. 28 is a front perspective view of the bracket of FIG. 27.
Figure 29:
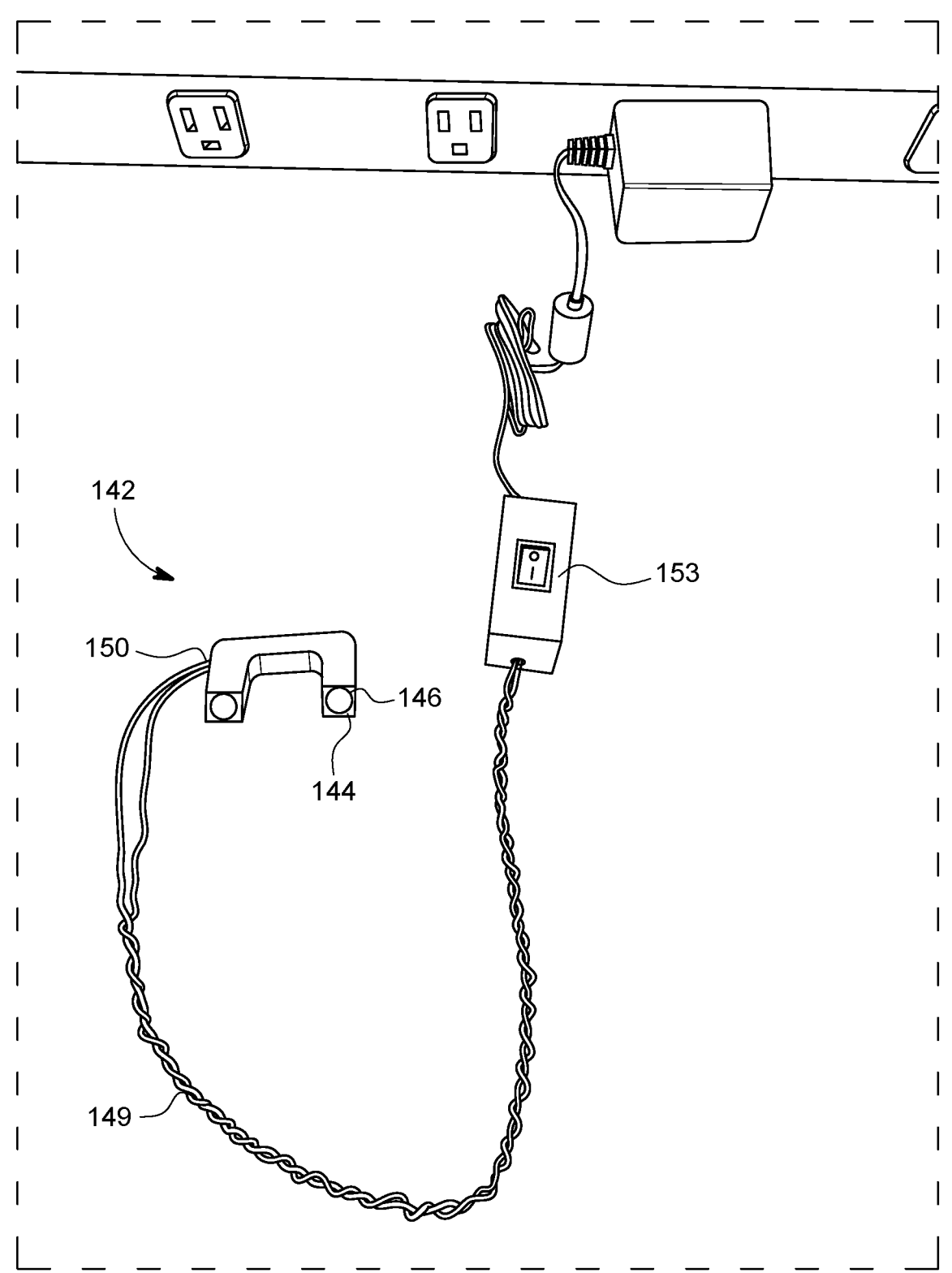
FIG. 29 is diagrammatic view of the components of a corded embodiment of a speculum light for use with the bracket of FIG. 27.
Figure 30:
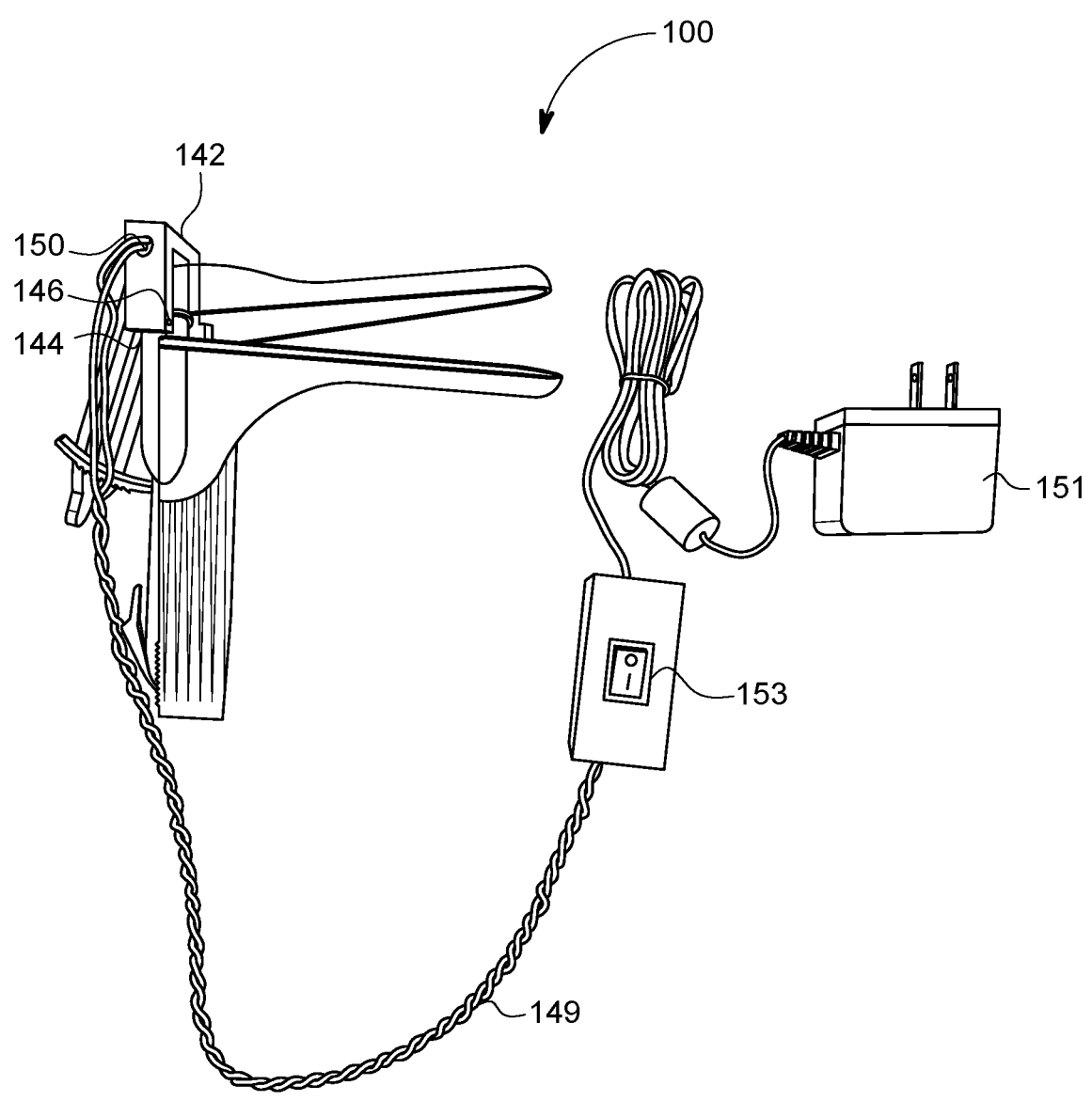
FIG. 30 is a diagrammatic view showing the components of FIG. 29 attached to a speculum.

As illustrated in FIGS. 25-26, the speculum may comprise a snap key 156. The snap key 156 may be fitted to an aperture or slot 262 on a lateral surface 254 of each of the first and second battery housings 126, 128. The cantilever snap key 156 may comprise a button 158 and a base member further comprising a first leg 160 and a second leg 162. The button 158 may comprise an oversized rounded, textured surface with tapered edges configured to be easily pressed by the user or clinician. Without limitation to shape, the first leg 160 may be substantially rectangular in form and positioned opposite the second leg 162. The second leg 162 may be substantially rectangular with a protrusion 164 extending outwards from a foot of the leg. The first and second legs 160, 162 of the snap key 156 may be inserted during manufacturing within the aperture 262 of the first and second battery housings 126, 128. The cantilever snap key 156 may be couplable at a snap-fit joint within the first and second battery housings 126, 128, wherein the protrusion 164 of the second leg 162 interlocks with a mating part within the first and second battery housings 126, 128.

The snap key 156 may be inserted into the aperture 262 in a first, inactive position. In the inactive position, the second leg 162 may be in a compressed or bent position. Insertion of the key 156 may be aided by an angled or rounded surface 264 on the protrusion 164. Embodiments of the speculum may be shipped with the snap key in the inactive position. In use, a user may engage the button surface 158 of the snap key and move the key from the inactive to an active position, When the snap key is moved to the active position, the key may engage a portion of a battery leads or a connector 266 to complete the electrical connection. As the snap key is moved into the active position, the second leg 162 may extend from its bent position, and a step or latch 268 formed on the protrusion 164 may engage and lock with a portion of the battery housing, thereby maintaining the lights in active state.

As illustrated in FIGS. 27-30, embodiments may comprise a corded light bracket 142 for use with a speculum. The light bracket may be reusable or disposable and intended for a single use. Embodiments of the corded light bracket 142 comprise compartments 144 for housing first and second light sources, which may be positioned within apertures 146 angled to converge the emitted light towards the centerline of the examination area. The corded light bracket 142 may be either coupled to or integrated with the yoke 106 in a U-shape and comprises inner channels 148 permitting wiring 149 to extend from the first and second light sources 118, 120 to be housed within the corded light bracket 142 and directed, towards a bridge of the corded light bracket 142 through an aperture 150. The wiring 149 may be attached to an intermediate plug and then to a power plug 151, such an AC/DC wall mount adapter that is couplable to an electrical outlet. The intermediate plug allows for disconnection of the corded light bracket from the power switch 153 and AC/DC wall mount plug 151 for cleaning purposes. The corded light bracket 142 may comprises a power switch 153 that toggles the first and second light sources 118, 120 on and off. It will be appreciated that the corded light bracket 142 may be a reusable component that is removably couplable to the first and second arms 110, 112 of the yoke 106. By contrast, the yoke 106, the handle 114, and the anterior and posterior blades 102, 104 may be disposable, single-use components.

Accordingly, a clinician, for example a urologist or other specialist that performs multiple pelvic exams or urological procedures, may open a disposable speculum and mount the corded light bracket 142 to first and second arms of a yoke of the speculum. After performing the pelvic exam or urological procedure, the clinician may discard the disposable speculum that has made contact with the patient or otherwise become soiled or contaminated. The clinician may discard the corded bracket if intended for single use or may clean and store the corded light bracket 142 for subsequent use if intended for reuse. Such corded embodiments of the disposable speculum 100 obviate the need for batteries and may be reused upon any necessary sterilization between patients in such environments as operating rooms, surgical centers, outpatient clinical offices, and OBGYN clinics. It is also contemplated that the wiring 149 may be alternatively coupled to a plug that allows disconnection from the power switch 153 and power plug 151 prior to cleaning of the reusable corded light bracket.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. A speculum, comprising:
an upper blade;
a lower blade positioned opposite the upper blade;
a yoke coupled to the upper blade and the lower blade, wherein the yoke comprises a first arm having a first light source mounted on an interior surface of the first arm and a second arm having a second light source mounted on an interior surface of the second arm;
a first battery housing comprising a compartment that encloses a first battery configured to supply power to the first light source, the first battery housing mounted on an exterior surface of the yoke first arm;
a second battery housing comprising a compartment that encloses a second battery configured to supply power to the second light source, the second battery housing mounted on an exterior surface of the yoke second arm;
a handle coupled to a base of the yoke; and
a yoke adjustment member coupled to the handle, the yoke adjustment member comprising a plurality of slots configured to engage a protrusion on the upper blade whereby the lower blade and upper blade may be articulated between a closed configuration and an open configuration.

2. The speculum of claim 1, wherein the first and second battery housings are configured to contain a Y-shaped pull tab that maintains the first and second light sources in an inactive state until the tab is removed from the speculum and the first and second light sources change to an active state.

3. The speculum of claim 1, wherein the first light source and the second light source are LED lights.

4. The speculum of claim 3, wherein the first light source and the second light source are angled inward towards the front of the speculum being configured to converge emitted light into a focused beam on an examination area.

5. The speculum of claim 1, wherein the yoke adjustment member comprises a soft polymer configured to reduce the sound of the speculum when articulated between a closed configuration and an open configuration.

6. The speculum of claim 1, further comprising a tab configured to prevent the operation of the first light source and the second light source until removed.

7. The speculum of claim 6, wherein the tab is a Y-shaped tab.

8. The speculum of claim 7, wherein the tab is removed from the speculum by pulling the tab in a direction parallel to the handle.

9. A speculum, comprising:
an upper blade;
a lower blade positioned opposite the upper blade;
a yoke coupled to the upper blade and the lower blade, wherein the yoke further comprises a first arm having a first light source mounted on an exterior surface of the first arm and a second arm having a second light source mounted on an exterior surface of the second arm;

a first battery housing configured to supply power to the first light source and comprising a slot formed in a wall of the first battery housing and a key inserted into the slot;

a second battery housing configured to supply power to the second light source;

a handle coupled to a base of the yoke; and a yoke adjustment member coupled to the ergonomic handle, the yoke adjustment member comprising a plurality of slots configured to engage a protrusion on the upper blade whereby the lower blade and upper blade may be articulated between a closed configuration and an open configuration;

wherein upon insertion into the housing, the key is secured in a first, inactive position at least partially within the first battery housing; and wherein the key is pushed from the first, inactive position to a second, active position at least partially within the first battery housing to activate the first light source.

10. The speculum of claim 9, wherein the first light source is housed within the first battery housing and the second light source is housed within the second battery housing.

11. The speculum of claim 9 further comprising a second slot formed in a wall of the second battery housing and a second key that is inserted into the second slot.

12. The speculum of claim 9 wherein the key is a snap key.

13. The speculum of claim 11, wherein upon insertion into the second battery housing, the second key is secured in a first, inactive position.

14. The speculum of claim 9, wherein a latch of the key engages the first battery housing to hold the key in the active position.

15. The speculum of claim 9, wherein the first light source and the second light source are angled inward towards the front of the speculum being configured to converge emitted light into a focused beam on an examination area.

\* \* \* \* \*